United States Patent [19]

Zucal et al.

[11] Patent Number: 4,481,297
[45] Date of Patent: Nov. 6, 1984

[54] VAPOR DETECTION TUBE AND METHOD OF TESTING FOR A VAPOR

[75] Inventors: Thomas A. Zucal, Richland; John D. McIntosh, Newfield, both of N.J.

[73] Assignee: Owens-Illinois, Inc., Toledo, Ohio

[21] Appl. No.: 377,764

[22] Filed: May 13, 1982

[51] Int. Cl.³ .................... G01N 1/22; G01N 31/06
[52] U.S. Cl. .................................. 436/181; 73/23; 73/863.21; 215/32; 422/59; 422/88; 436/167
[58] Field of Search .................. 73/863.21, 863.23, 23; 422/58, 59, 60, 86, 88, 83; 215/32; 436/167, 181

[56] References Cited

U.S. PATENT DOCUMENTS

| | | | |
|---|---|---|---|
| 2,908,555 | 10/1959 | Grosskopf | 422/86 |
| 3,204,835 | 9/1965 | Michel | 215/32 X |
| 3,388,975 | 6/1968 | Wallace | 422/86 X |
| 3,507,623 | 4/1970 | McConnaughey | 422/86 |
| 3,676,073 | 7/1972 | Luckey | 436/181 X |
| 3,749,271 | 7/1973 | Ellis, Jr. et al. | 215/32 |

FOREIGN PATENT DOCUMENTS 970059  9/1964  United Kingdom ............ 73/863.21

Primary Examiner—Arnold Turk
Attorney, Agent, or Firm—John R. Nelson; Myron E. Click

[57] ABSTRACT

A vapor detection tube is disclosed, the tube holding an adsorbent material for adsorbing vapors, the tube having at least one end with a constriction near the end and the diameter at the far end of the tube being of about the same diameter as the main portion of the tube. There is disclosed plastic sealing caps for sealing the ends of the tube for safe and contamination free handling and shipping, the tube being so constructed and arranged that it can be easily broken at the constriction in a clean and uniform manner to provide an open tube for sampling and the tube being easily sealed by sealing members after the sampling is finished and before analysis is made.

7 Claims, 4 Drawing Figures

VAPOR DETECTION TUBE AND METHOD OF TESTING FOR A VAPOR

The present invention is directed to a vapor detection tube for holding an adsorbent material for adsorbing vapers, the tube being adapted for sampling and having means for sealing the ends of the tube for safe handling and shipping.

Vapor detection tubes with breakable end tips have been used for collecting vapor samples from air, the tubes containing therewithin high activity sorbents such as charcoal for the vapors. Generally the tube is used by breaking off the tips of the tube, placing the tube in a pump line, pulling gas through the tube where the chemical vapor is trapped in the sorbent. Following the collection period, the tube is generally sealed and taken to a laboratory where the contents of the tube are removed and the chemical vapor is solvent-extracted from the tube. The resulting solutions are then analyzed to determine the amount of chemical vapor present.

In the vapor testing procedure, when using a detection tube, there is a need for uniform and reproducible sampling conditions including pulling a uniform and consistent rate of gas within the tube through the tube. There is also a need for means to keep the adsorbents and inside of the tube clean and protected after manufacture for shipping and handling.

It is an object of the present invention to provide a vapor detection tube having a main portion and two end portions, a constriction between the main tube portion and each end portion, and a score line or other method of stress concentration at the constriction for the easy and safe breaking in a uniform and clean manner for subsequent sampling, there being a clean uniform opening left after breaking, and sealing means for sealing each end of the tube to protect the same after manufacture.

It is an object of the present invention to provide a method for testing for a vapor using a tube having a main tube portion and a first end with a constriction between the main tube portion and an end, the tube having a second end adapted for sealing, the method comprising the steps of:

A. removing the sealing means from the first end of the tube;
B. breaking uniformly and cleanly the first end of the tube at the constriction to provide a uniform opening for consistent air sampling;
C. opening the second end of the tube;
D. inserting the tube in the sampling line; and
E. collecting a vapor sample for testing.

These and other objects of the patent specification that follows, the appended claims and the drawings in which:

Figure 1:
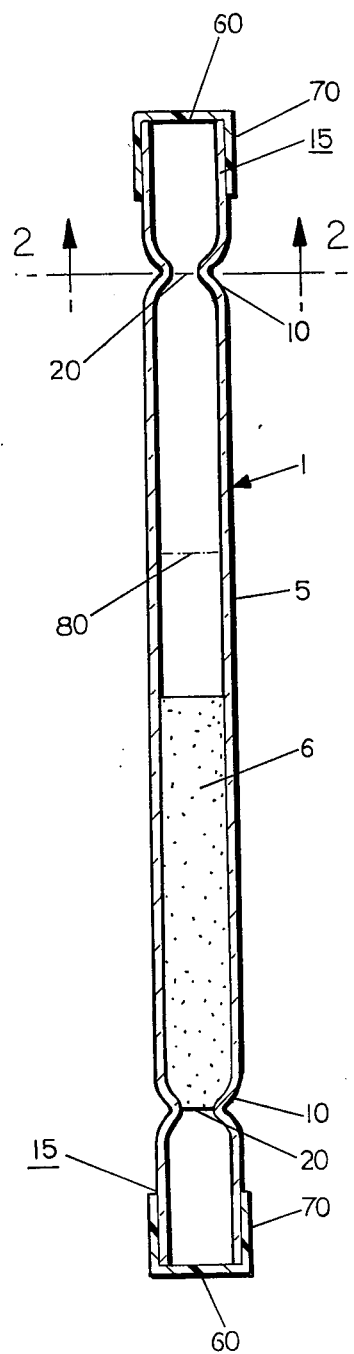
FIG. 1 is a side elevational view of a vapor detection tube of the present invention.
Figure 2:
FIG. 2 is a cross-sectional view of the tube of FIG. 1.

The present invention provides an outstanding vapor detection tube that can be handled quite safely for shipping and subsequent testing.

The present invention provides a vapor detection tube for holding an adsorbent material for adsorbing the vapors, the tube having at least one end with constriction near the end thereof, the tube having open ends, there being plastic or rubberized sealing caps for sealing the ends of the tube for safe handling and for safe shipping and to prevent contamination, the tubes being so constructed and arranged that they can be easily broken at the constriction in a clean and uniform manner to provide an open tube for sampling at a consistent rate. The tube is adapted for sealing after sampling by a sealing cap on each end.

The present invention also provides a vapor detection tube that preferably has each end of the tube provided with a constriction and each end being sealed to prevent contamination and to provide an efficient and safe tube for shipping and for analysis merely by removing the seals at each end.

The present invention provides a method for testing for a vapor using a vapor detection tube comprising an adsorbent inside and the tube having a constriction near each end thereof, each end of the tube being open, there being sealing means for sealing the ends of the tube for safe handling and for safe shipping, the method comprising the steps of:

A. removing the sealing means from each end of the tube;
B. breaking the first end of the tube at the constriction to provide an open tube for testing;
C. opening the second end of the tube; and
D. drawing a sample through the tube to collect a sample inside the tube on the adsorbent.

The present invention also provides the further steps of sealing both ends of the tube after analysis, and breaking the tube open at a break position in the middle portion for analysis in a laboratory.

As seen in the drawings, a vapor detection tube 1 is shown having a main tube portion 5 containing an adsorbent 6 such as charcoal and two ends 15. Located near at least one of the ends is a constriction 10 having a score line or other stress concentration 20 for easy and safe breaking to provide a clean and uniform opening 30 for efficient and convenient sampling.

As seen in the preferred embodiment shown in FIG. 1, the tube has two open ends 60. Sealing means 70 that is preferably a tightly fitting plastic cap, such as a heat shrink cap, is provided to protect the ends and inside of the tube after manufacture and during shipment. After shipment, the tube is easily prepared for use in a sampling pump line by removing the caps 70 and breaking the tube near each end at the constriction 10.

The sealing means can conveniently be a plastic cap of polyethylene, polypropylene, polystyrene, or other material that provides a durable, impact resistant protective cover to contamination, air, dirt and accidental rough handling.

Figure 4:
FIG. 4 is an end view of the tube showing the clean and uniform opening at the broken end of the tube.
Figure 3:
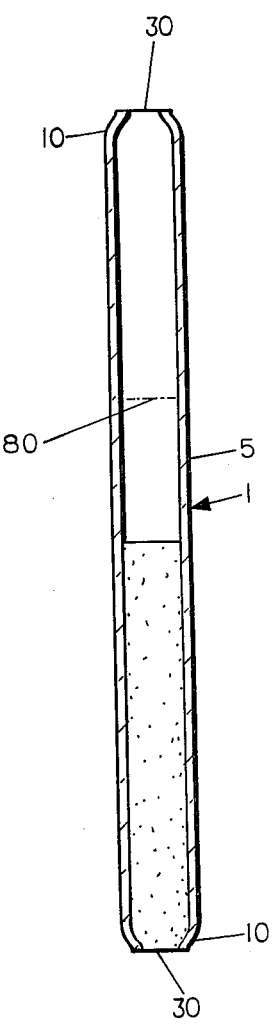
FIG. 3 is a side elevational view of the vapor detection tube of FIG. 1 after the ends have been broken at each of the constrictions.

When broken, as shown in FIGS. 3 and 4, a clean and uniform opening is provided at each end of the tube. The uniform opening helps provide a uniform sampling rate from tube to tube.

A score line 80 or other stress concentration break position is provided in the main tube portion 5 so that the tube can be broken easily after sampling in preparation for analysis.

What is claimed is:

1. A vapor detection tube having inside an adsorbent material for adsorbing vapors, the tube having ends in which each end has a constriction near the end and a diameter at the end about the same as the diameter of a middle portion of the tube, a sealing means comprising a heat shrunk plastic cap for sealing each end of the tube for safe handling and shipping, the cap closing each end of the tube and extending inwardly from each tube end for a distance less than the distance to the constriction, the tube so constructed and arranged that it can be easily broken at each constriction in a clean and uniform manner to provide an open tube with clean, precise uniform openings for accurate sampling, and the tube being easily sealed by a second sealing member after the sampling is finished and before analysis is made.

2. A tube as defined in claim 1 in which there is a stress concentration position in the middle tube portion for easy breaking for analysis.

3. A method for collecting for subsequent testing a vapor using a vapor detection tube comprising a glass tube having an adsorbent inside, the tube having a middle portion and first and second ends with a constriction near each end and the ends of the tube being open, and there being heat shrunk plastic cap sealing means for sealing the first and second ends of the tube for safe and contamination free handling, the method comprising the steps of:

A. removing easily and cleanly the cap sealing means from each end of the tube to provide a clean end free from shipping and handling damage;
B. breaking uniformly and cleanly the first and second ends of the tube at each constriction to provide an open tube for sampling with a clean, precise and uniform opening at each end;
C. placing the tube in a sampling line; and
D. drawing a sample through the tube to collect a clean and uniformly-drawn sample inside the tube on the adsorbent.

4. A method as defined in claim 3 in which there is provided the further steps of:
(E) sealing both ends of the tube; and
(F) breaking the tube open at a stress concentrated position in the middle tube portion for analysis.

5. A method as defined in claim 4 in which there is a score line at the constriction and a score line at the stress concentrated position in the middle tube portion.

6. A method for collecting for subsequent testing a vapor using a vapor detection tube comprising having an adsorbent inside a glass tube having a first end with a constriction near the end, there being a second tube end with a constriction near the end and the second end being of about the same diameter as a middle portion of a tube, the ends of the tube being open and there being heat shrunk plastic cap sealing means for sealing the first and second ends of the tube for safe and contamination free handling, the method comprising the steps of:

A. removing the cap sealing means from each end of the tube to provide clean tube ends;
B. breaking uniformly and cleanly the first end of the tube at the constriction to provide an open tube for sampling, the opening being precisely made to provide a clean uniform opening;
C. breaking uniformly and cleanly the second end of the tube at the constriction, the opening being precisely made to provide a clean and uniform opening;
D. drawing a sample through the tube to collect a sample inside the tube on the adsorbent.

7. A method as defined in claim 6 in which there is provided the further steps of:
(E) sealing both ends of the tube; and
(F) breaking the tube open at a stress concentrated position at the middle tube portion for analysis.

* * * * *